US010881508B2

United States Patent
Snyders

(10) Patent No.: US 10,881,508 B2
(45) Date of Patent: Jan. 5, 2021

(54) LIFETIME REGENERATIVE HEART VALVE

(71) Applicant: Robert V. Snyders, Ballwin, MO (US)

(72) Inventor: Robert V. Snyders, Ballwin, MO (US)

( * ) Notice: Subject to any disclaimer, the term of this patent is extended or adjusted under 35 U.S.C. 154(b) by 48 days.

(21) Appl. No.: 15/739,975

(22) PCT Filed: Jun. 30, 2016

(86) PCT No.: PCT/US2016/040366
§ 371 (c)(1),
(2) Date: Dec. 26, 2017

(87) PCT Pub. No.: WO2017/004360
PCT Pub. Date: Jan. 5, 2017

(65) Prior Publication Data
US 2018/0185144 A1 Jul. 5, 2018

Related U.S. Application Data

(60) Provisional application No. 62/186,893, filed on Jun. 30, 2015.

(51) Int. Cl.
A61F 2/24 (2006.01)
(52) U.S. Cl.
CPC .......... *A61F 2/2418* (2013.01); *A61F 2/2412* (2013.01); *A61F 2/2409* (2013.01); *A61F 2250/0082* (2013.01)
(58) Field of Classification Search
CPC ................................ A61K 35/28; A61K 38/30
See application file for complete search history.

(56) References Cited

U.S. PATENT DOCUMENTS

| 8,874,204 B2 | 10/2014 | Sih | |
| 2012/0209379 A1* | 8/2012 | Shaolian | A61F 2/2445 623/2.37 |
| 2014/0023723 A1* | 1/2014 | Leach | A61L 27/3633 424/577 |

FOREIGN PATENT DOCUMENTS

| EP | 0170262 A2 * | 2/1986 | ........... A61F 2/2412 |
| EP | 0170262 A2 | 5/1988 | |
| WO | 201318217 A1 | 12/2013 | |

* cited by examiner

Primary Examiner — Yashita Sharma
(74) Attorney, Agent, or Firm — David E. Crawford; Crawford I.P. Law

(57) ABSTRACT

A replacement valve for replacing a damaged heart valve having a plurality of cusps separating an upstream region from a downstream region of a passage. The replacement valve includes a flexible band having biocompatible scaffolding sized for contact with a wall surrounding the passage in the patient's heart. The valve includes a resilient element attached to the flexible band for expanding the flexible band to contact the wall of the passage. The valve includes regenerative struts spaced around the flexible band. Each strut extends from an outboard end joined to an inward face of the flexible band to a central end. The central ends of the struts are joined together. The valve includes a flexible regenerative membrane joined to adjacent struts. The membrane extends outboard to an inward face of the band. An outboard edge of the membrane is free to move between a closed position and an open position.

15 Claims, 8 Drawing Sheets

LIFETIME REGENERATIVE HEART VALVE

BACKGROUND

The present invention relates generally to biomechanical valve implants, and more particularly to regenerative heart valves for replacing damaged heart valves.

A human heart has four chambers which alternately expand and contract to pump blood through the vessels of the body. The heart also includes a check valve at the upstream end of each chamber to ensure that blood flows in a correct direction through the body as the heart chambers expand and contract. These valves sometimes are malformed or become damaged, resulting in their inability to close when the downstream chamber contracts. When a valve does not close, blood flows backward through the valve, resulting in diminished blood flow and lower blood pressure. The valves can also become damaged so they do not open sufficiently, which also results in diminished downstream blood flow.

Many mechanical and bioprosthetic valves have been developed to replace native heart valves. Some of these prior valves are discussed in U.S. Pat. No. 6,540,782 entitled, "Artificial Heart Valve," and U.S. Pat. No. 6,821,297 entitled, "Artificial Heart Valve, Implantation Instrument and Method therefor," both of which are incorporated in their respective entireties in the present disclosure by reference. Both of these patents are directed in part to advancements in artificial heart valves having a construction sometimes referred to as a tri-leaflet Funnel Valve (FV).

Prior funnel valves include a metal frame constructed of U-shaped wires joined at their centers. The wires are angularly spaced at their junction so the frame is dome-shaped, having opposite concave and convex sides. Anchors (e.g., hooks) are formed at the ends of each wire to attach the wires to muscle forming a passage in the heart. In use, the frame is oriented so its convex side faces upstream. A band of biocompatible synthetic material extends around an inside and an outside of the frame adjacent the anchors so an outboard face of the band abuts the heart muscle forming the passage (i.e., the annulus or valve ring) and an inboard face provides a continuous surface around the inside of the frame. Three flexible synthetic or heterologous tissue leaflets are attached to the frame. Each leaflet is generally triangular, having an inboard corner attached to the center of the frame. The leaflets extend downstream and outward from the center of the frame to opposite outboard corners attached to the inboard face of the band. The outboard edge of each leaflet, which extends between the outboard corners, is free to flex inward, creating an opening between the outboard edge and the band. The leaflet flexes outward to seal against the band. The leaflet also flexes inward when fluid pressure upstream from the valve is greater than downstream pressure and flexes outward when downstream pressure is greater than upstream pressure. Thus, blood flows through the funnel valve in only one direction.

Although valves and surgical procedures have been developed to replace damaged or malformed heart valves, they have significant drawbacks. Many bioprosthetic valves have limited lifespans (e.g., about 10-15 years) and must then be replaced during a second operation. Because the comorbid risk of such operations increases with age, multiple operations are undesirable, not only due to the increased risk of death, but also the emotional stresses associated with the increased risk. Thus, there is a need for a replacement valve having a lifespan equivalent to that of the patient.

Further, valves replaced in infants and small children do not grow with the child, resulting in a need to replace the replacement valve with a larger valve when the child outgrows the prior replacement valve. Depending on the size of the child when the original valve is replaced, the child may need multiple surgeries through his or her lifetime. Thus, there is a need for a replacement valve that eliminates the necessity for replacement.

SUMMARY

In one aspect, a replacement valve for replacing a damaged heart valve comprises a flexible band including biocompatible scaffolding sized for contact with a wall surrounding the passage in the patient's heart. Further, the valve comprises a resilient element attached to the flexible band for expanding the flexible band to contact the wall of the passage. In addition, the valve comprises a plurality of regenerative struts spaced around the flexible band. Each strut extends from an outboard end joined to an inward face of the flexible band to a central end. The central ends of the struts are joined together. The valve also comprises a flexible regenerative membrane joined to adjacent pairs of the struts. The membrane extends outboard to an inward face of the band. An outboard edge of the membrane is free to move between a closed position in which the membrane abuts the inward face of the band to prevent fluid flow past the membrane and an open position in which the outboard edge of the membrane is spaced from the inward face of the band to permit fluid flow past the membrane.

In another aspect, a replacement valve for replacing a damaged heart valve comprises a flexible band including biocompatible scaffolding sized for contact with a wall surrounding the passage in the patient's heart. Further, the valve comprises a plurality of regenerative struts spaced around the flexible band. Each strut extends from an outboard end joined to an inward face of the flexible band to a central end. The central ends of the plurality of struts are joined together. The valve also comprises a flexible, cone-shaped, regenerative membrane joined to adjacent pairs of the plurality of struts. The membrane has an outer edge sized to correspond with an inward face of the band. At least portions of the outer edge of the membrane are free to move between a closed position in which the membrane abuts the inward face of the band to prevent fluid flow past the membrane and an open position in which the outer edge membrane is spaced from the inward face of the band to permit fluid flow past the membrane.

Other aspects of the present invention will be apparent in view of the following description and claims.

BRIEF DESCRIPTION OF THE DRAWINGS

Corresponding reference characters indicate corresponding parts throughout the drawings.

DETAILED DESCRIPTION OF THE DRAWINGS

Figure 1:
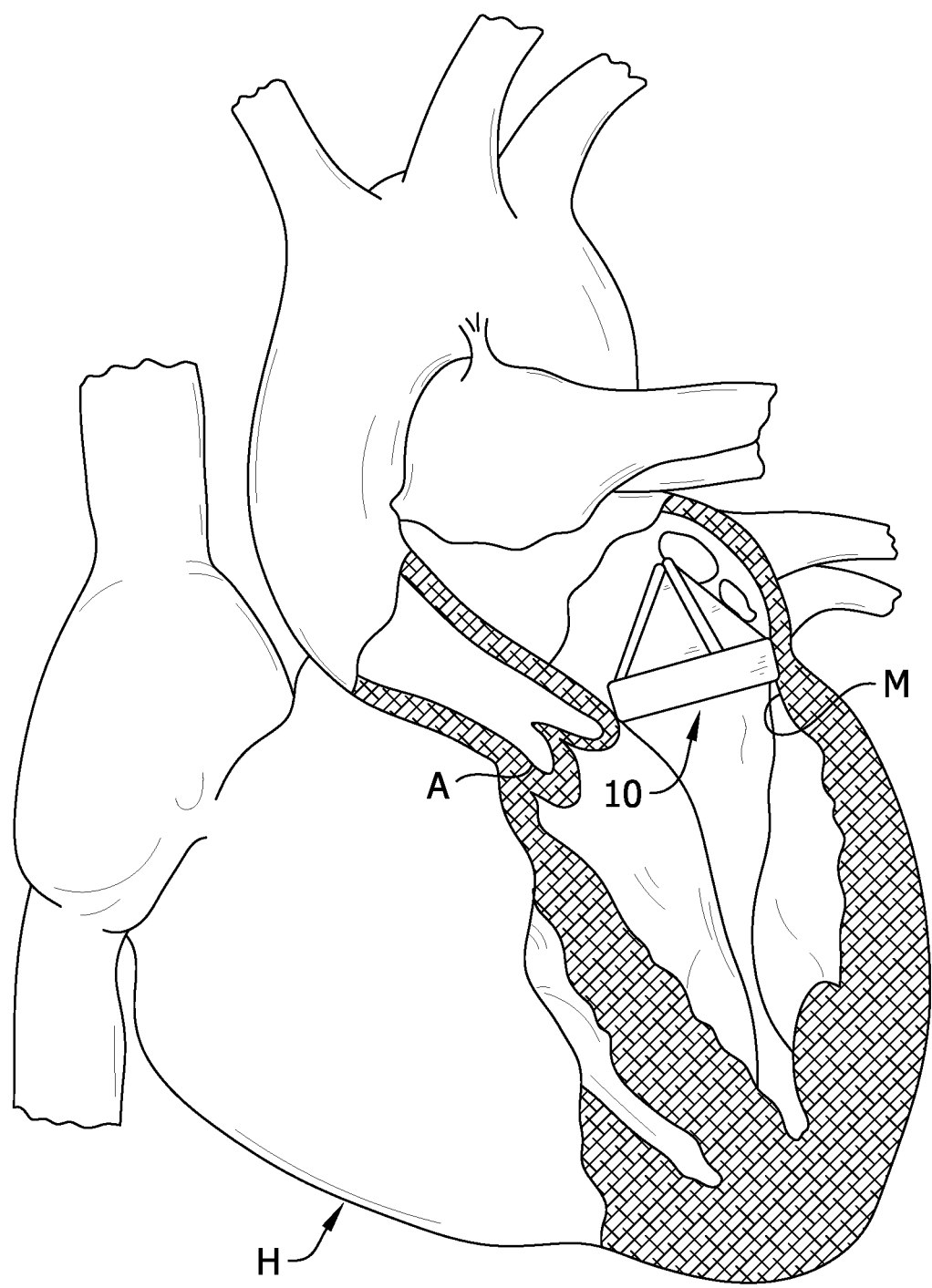
FIG. 1 is an elevation of a heart in partial section showing a replacement valve.

Referring to the drawings and in particular to FIG. 1, a lifetime regenerative heart valve or replacement valve of this disclosure is designated in its entirety by the reference number 10. The valve 10 is specifically configured for replacing a damaged mitral valve M of a heart, generally designated by H. The replacement valve 10 may have various sizes and configurations. For example, the valve 10 may be sized and configured to replace a damaged aortic valve A, pulmonary heart valve (not shown), or tricuspid heart valve (not shown). Regenerative materials are a group of materials including engineered tissues capable of self-healing that allow the body uses its own systems, with or without foreign biological materials, to recreate cells and rebuild tissues and organs. Engineered tissues evolved from the field of biomaterials development and refers to the practice of combining scaffolds, cells, and biologically active molecules into functional tissues. Tissue engineering is used to assemble regenerative materials that restore, maintain, or improve damaged tissues or whole organs. Those skilled in the fields of medicine, medical materials, and tissue engineering will appreciate the full scope of the term regenerative consistent with this usage.

Figure 2:
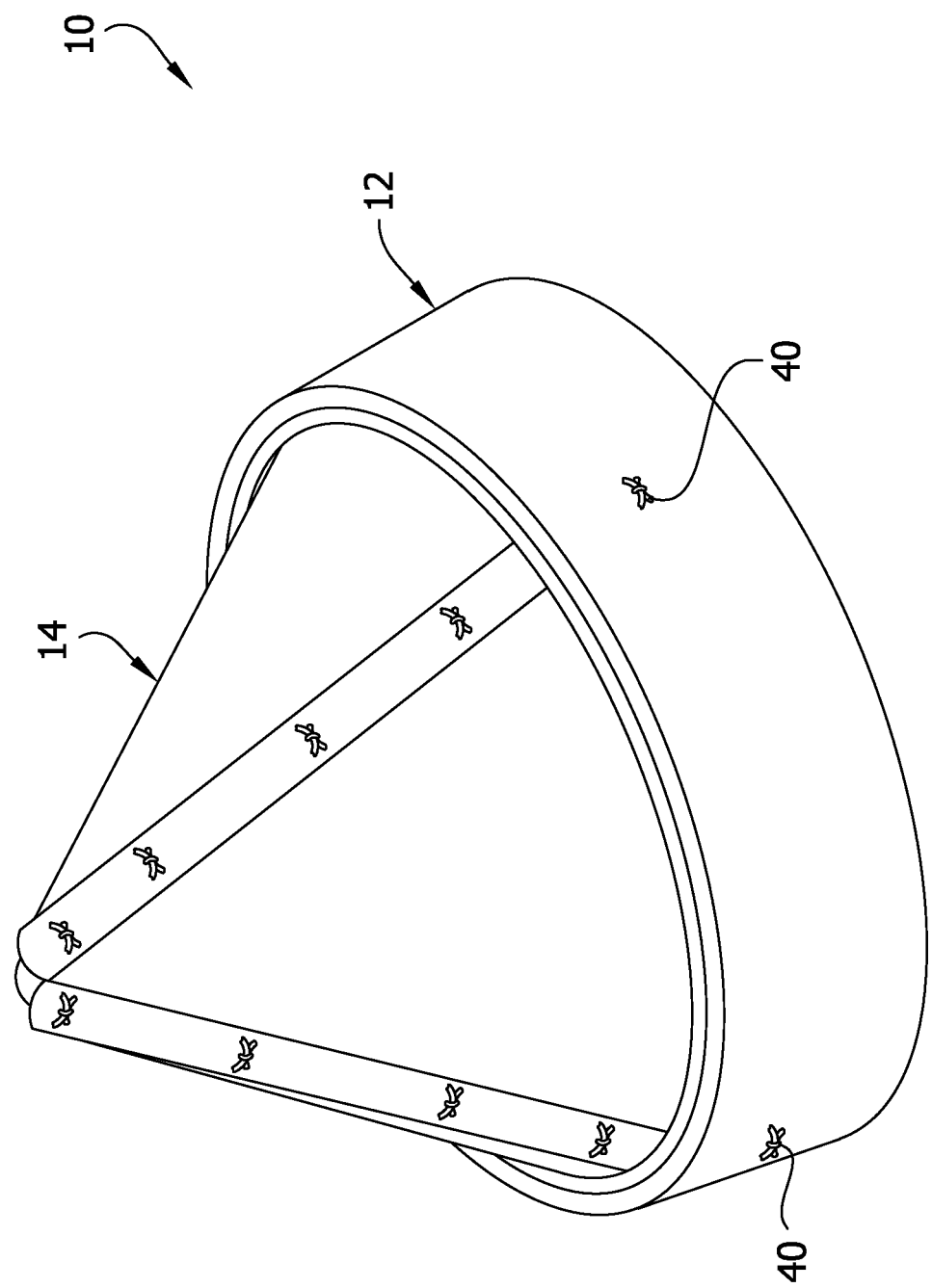
FIG. 2 is a perspective of a replacement valve having leaflets in a closed configuration.
Figure 3:
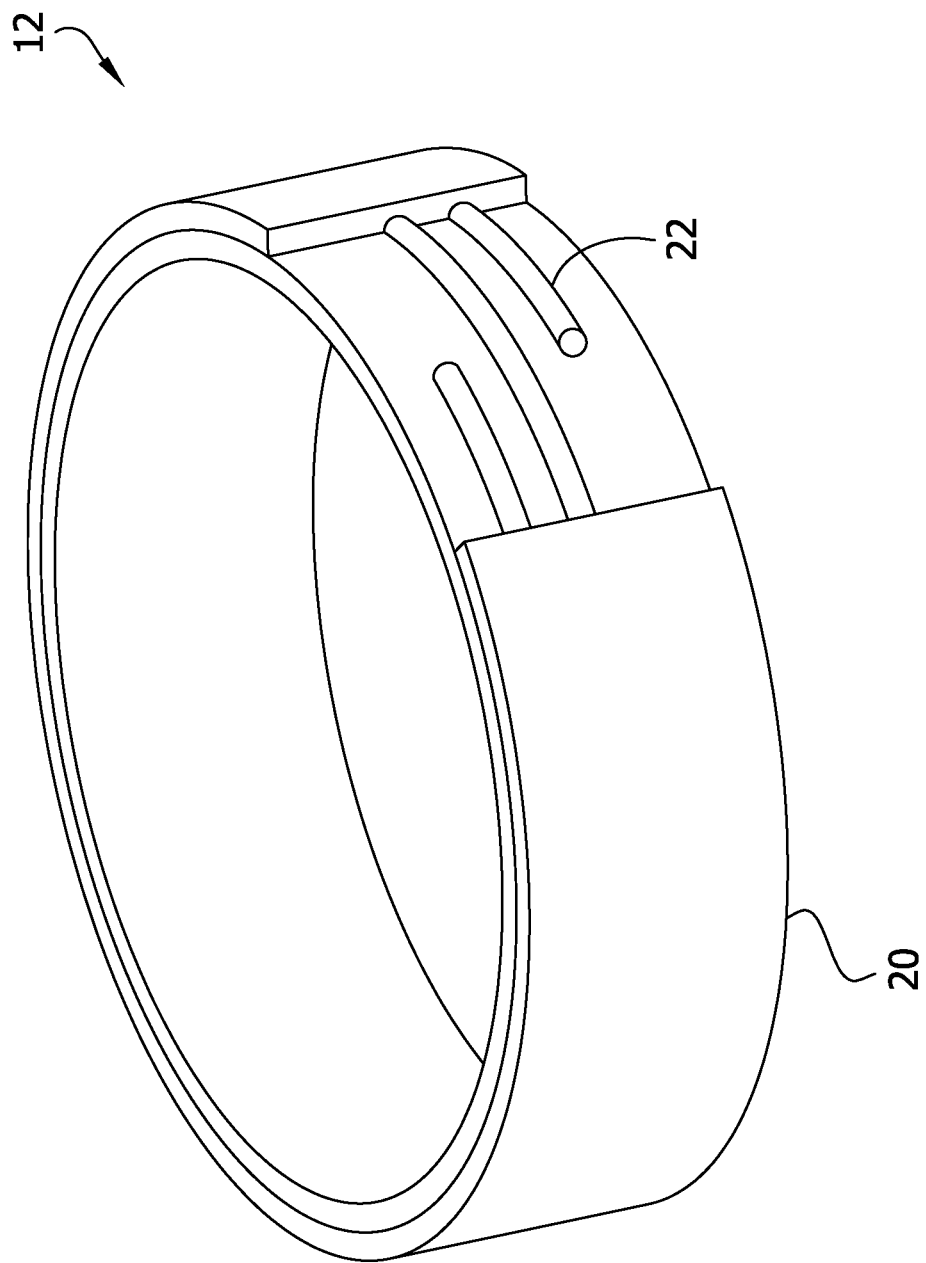
FIG. 3 is a fragmentary perspective of a collar of the replacement valve.

As illustrated in FIG. 2, the replacement valve 10 comprises a flexibly resilient collar, generally designated by 12, and a leaflet unit, generally designated by 14. As shown in FIG. 3, the collar 12 is formed from a flexible band 20 supported in its generally tubular configuration by a resilient stiffening loop 22. In one example, the loop 22 is biocompatible fiber (e.g., absorbable poly-1 lactic acid strips) formed in a coil. Loops 22 having other shapes (e.g., a circular or ovoidal ring) are also envisioned. In one example, the loop 22 may have a configuration similar to an Ella esophageal stent. Ella is a trademark of ELLA-CS, s.r.o. of the Czech Republic. The loop 22 has a diameter generally equal to the mean diameter of the passage in which the replacement valve is to be used. The band 20 comprises one or more plies of bioscaffold material lining the inside of the coil and one or more plies of bioscaffold material surrounding the coil. Although the band 20 may have other thicknesses, in one example, the band is about 3 mm. As will be appreciated by those skilled in the art, the collar 12 may be compressed to a size sufficient to be positioned in the passage and returns to its original, undeformed size at body temperature under the influence of the resilient loop 22 embedded in it. It is envisioned that in some examples the loop 22 may be omitted from the collar 12. In one example, the collar 12 has an outer diameter of about 28 mm. As will be appreciated, the loop 22 facilitates construction of the valve 10 by stiffening the collar 12.

The bioscaffold material of the band 20 permits surrounding native tissue to grow into the band by biogenesis so the band becomes an integral part of the native tissue. In pediatric use, it is envisioned that the band 20 will integrate with the native tissue so the collar 12 enlarges with the native heart passage as the patient grows. Such bioscaffold material may be made of any biocompatible material that supports biogenesis with blood cells and surrounding tissue.

Although synthetic bioscaffold materials are envisioned, in general, current materials include regenerative tissue-based materials comprising harvested cellular and matrix elements. These materials may be harvested from the patient (i.e., autologous) for regeneration using tissue culture techniques to provide an enhanced bioscaffold population of tissues. In some studies, selective primordial, pluripotent cells such as bone-marrow-derived mesenchymal stem cells from the patient have been isolated. Regenerative methods of incubated cell culture procedures have expanded the cellular counts onto viable bioscaffolds that can be converted into stable geometric designs suitable for various cardiovascular site applications including heart valve constructions. Alternatively, such bioscaffold material may comprise heterologous decellularized extracellular matrix (ECM) materials derived from allogeneic sources (e.g., small intestine submucosa piglet membranes). The ECM materials may be made in strips or sheets and maintained in a lyophilized (e.g., freeze-dried) condition for safe storage. Before being used to make heart valve components, the material is rehydrated with sterile saline. As will be appreciated by those skilled in the art, when implanted in a patient these materials are repopulated with host tissue by cellular regenerative repopulation assisted by enhanced blood vessel growth (i.e., revascularization) due to the geometry and positioning of the replacement valve. In other words, as blood flows through the material, host tissue forms in the scaffold. Thus, the tissue becomes genetically identical to the host regardless of whether it is harvested from the patient or made from another source. One suitable bioscaffold ECM material is available from CorMatrix Cardiovascular, Inc. of Atlanta, Georgia.

Figure 4:
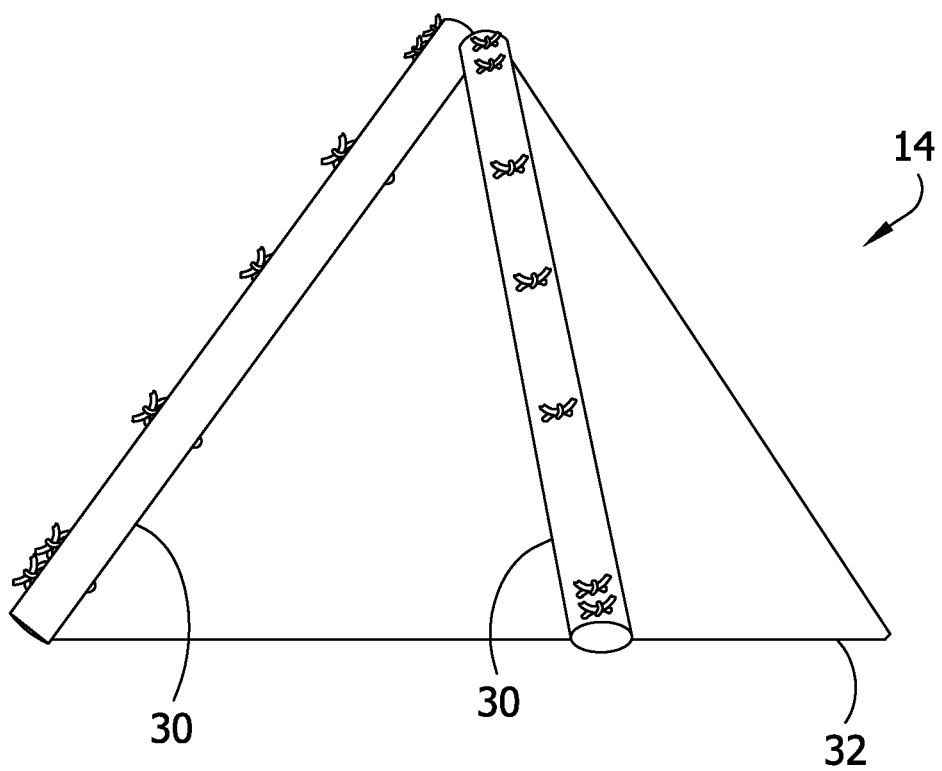
FIG. 4 is an elevation of a leaflet unit of the replacement valve.
Figure 5:
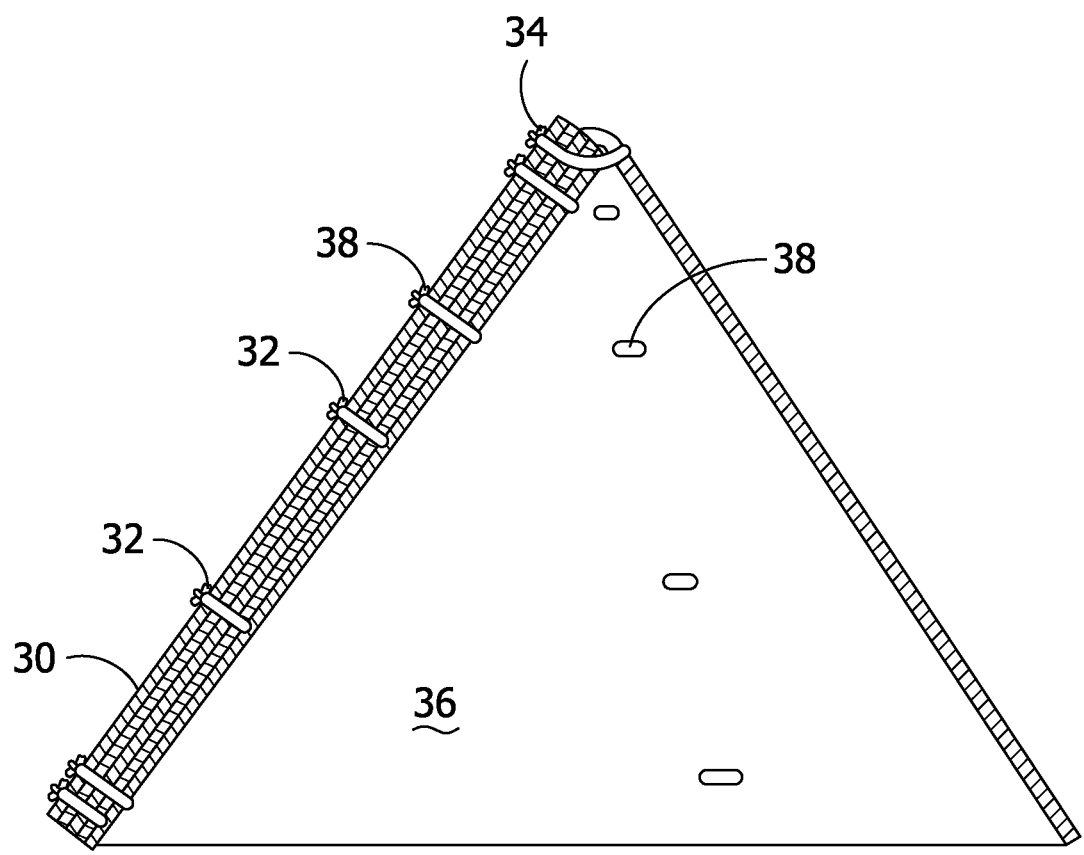
FIG. 5 is a vertical cross section of the leaflet unit.

As illustrated in FIGS. 4 and 5, the leaflet unit 14 comprises regenerative struts 30 formed as a three-dimensional truss structure. Each strut 30 is formed by rehydrating ECM membrane(s) with saline solution, rolling the membrane into an elongate strut, and fastening the membrane in the rolled configuration, such as with resorbable sutures 32 (e.g., polydioxanone sutures). The individual struts 30 are joined at a central node, such as with additional resorbable sutures 34. Although the assembled struts may have other dimensions, in some examples the struts have a thickness in a range of about 1 mm to about 3 mm, and a length of about 25 mm. Although other numbers of struts may be assembled, in one example three struts are joined at the central node.

A sheet of regenerative membrane 36 (e.g., one ply ECM material) is cut to a particular size corresponding to the struts 30. The cut membrane is formed as a cone and joined to the struts, such as with resorbable sutures 38. In one example, the membrane 36 is cut so it has about 5° of overlap for suturing. And, the cone is sized so the outer perimeter of the base of the cone matches the inner perimeter of the collar 12 during valve closure. In some examples the cone is sized so the outer perimeter of the base of the cone is generally equal to or at least as large as a perimeter of the inner face of the band 20 forming the collar 12. Although the struts 30 may be spaced differently when joined to the membrane 36, in some examples the struts are spaced evenly at about 120° intervals. By using a unitary membrane for the leaflets, it is easier to make the leaflet unit 14 and the position and size of each leaflet are more precise than might be achieved if the leaflets where non-unitary (i.e., formed as separate pieces and joined to form the unit). Although the membrane may have other dimensions, in some examples the membrane has a thickness in a range of about 0.005 inch to about 0.010 inch.

Figure 6:
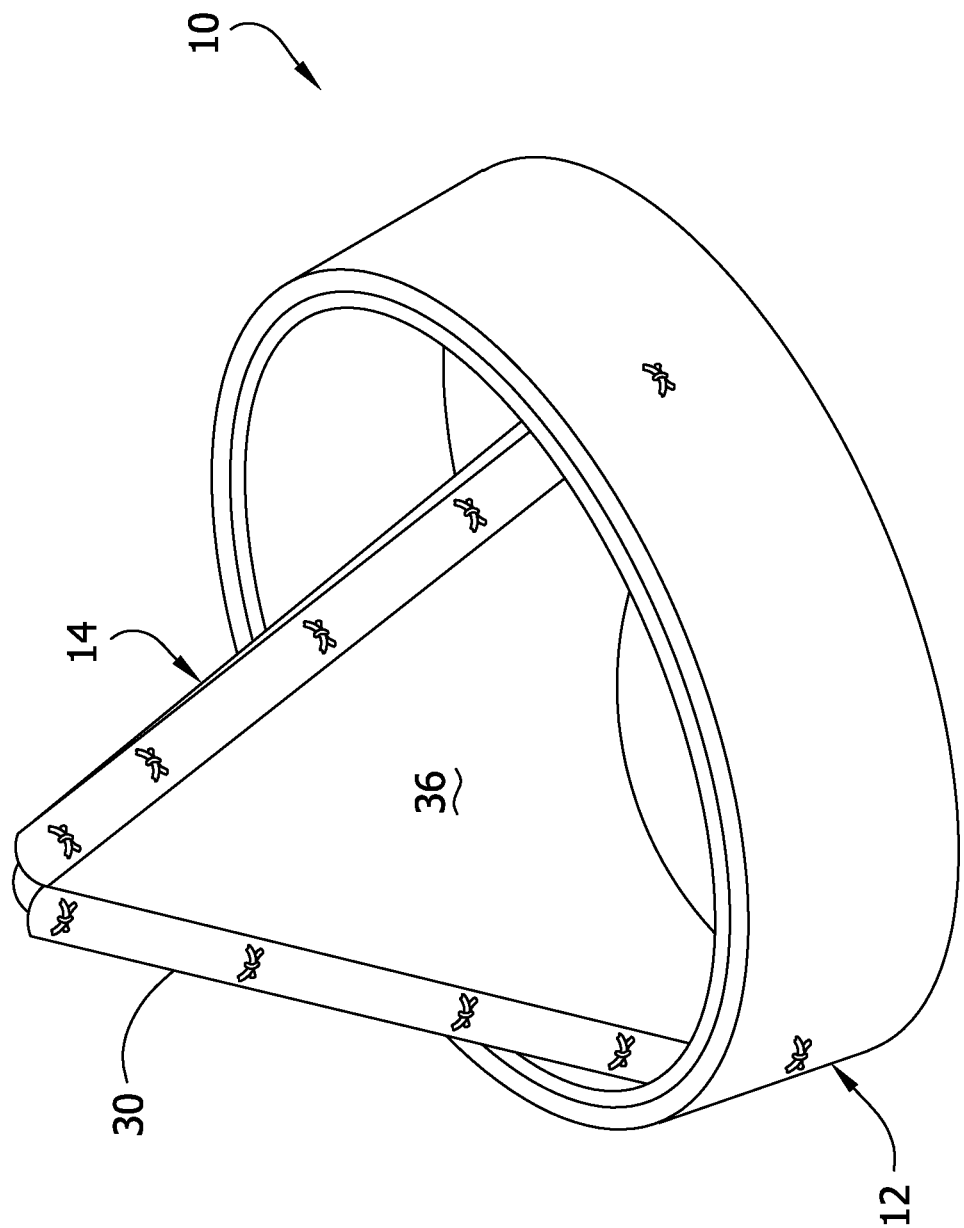
FIG. 6 is a perspective of the replacement valve of FIG. 2 having leaflets in an open configuration.
Figure 7:
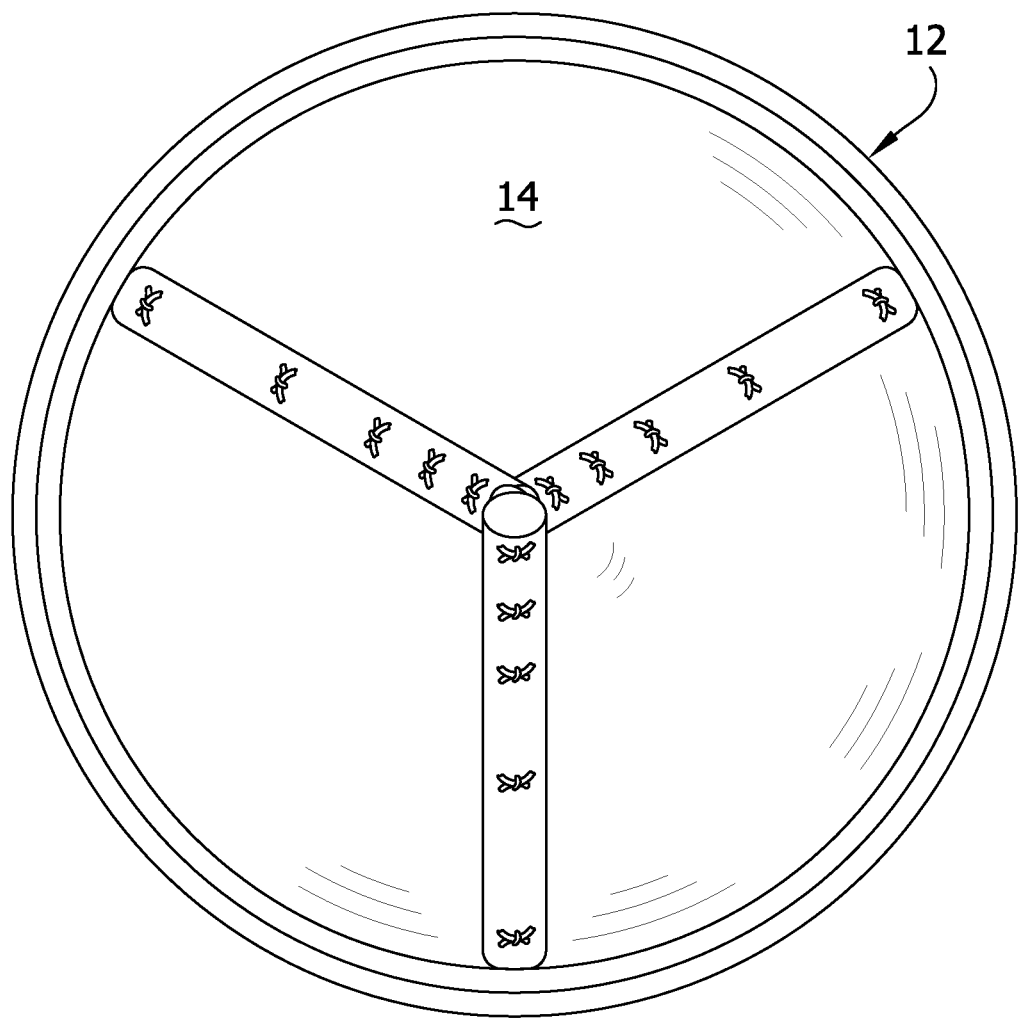
FIG. 7 is a plan of the replacement valve having leaflets in a closed configuration.
Figure 8:
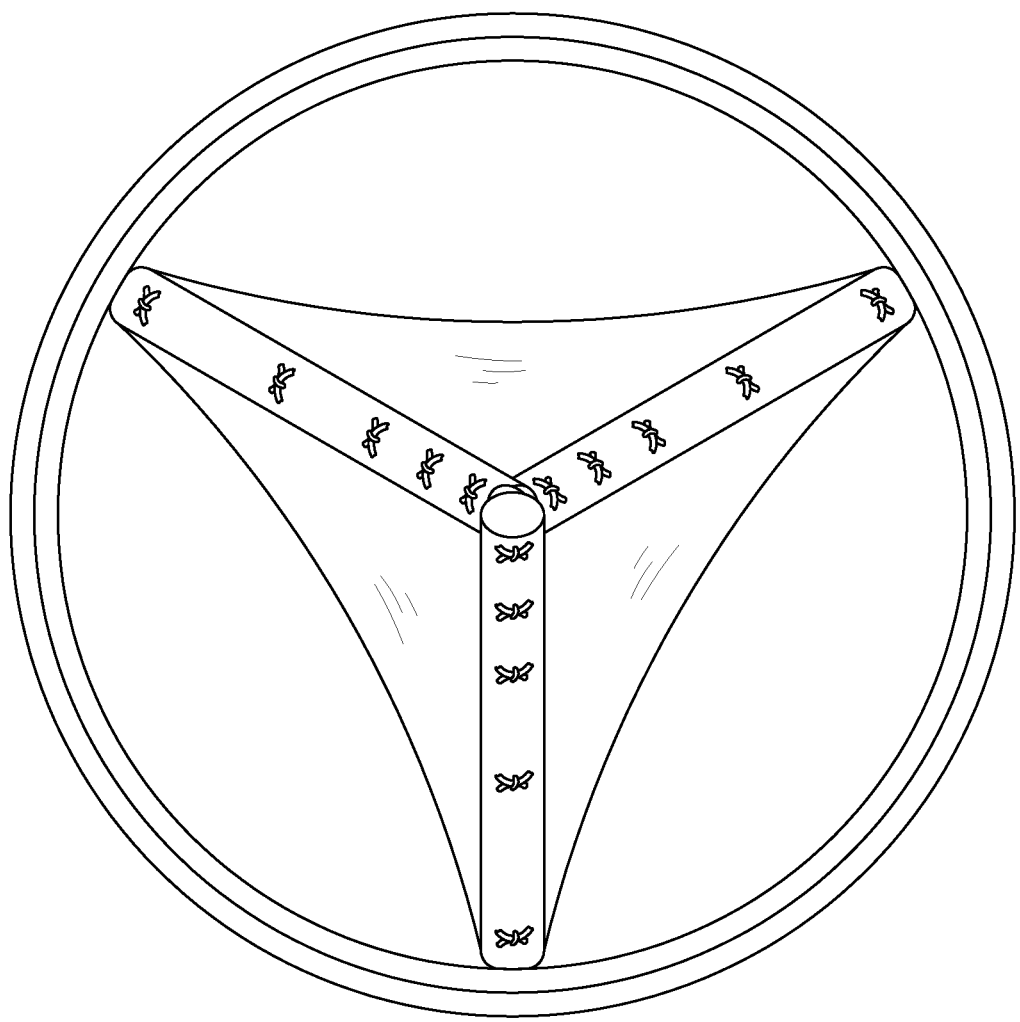
FIG. 8 is a plan of the replacement valve of FIG. 7 having leaflets in an open configuration.

The outboard end of each strut 30 is fastened to the collar 12 such as with resorbable sutures 40 as shown in FIG. 2 so the outboard or outer edge of the unitary membrane 36 is not connected to the band and is free to move relative to the band. Thus, the completed valve structure as shown in FIGS. 2 and 7 behaves differently than many artificial valves. When the pressure upstream from the valve 10 is greater than pressure downstream from the valve, the membrane 36 flexes inward toward a valve axial centerline to a position in which the outboard edge of the membrane is separated from the band 20 as shown in FIGS. 6 and 8. In this membrane configuration, the valve 10 is open. And, when the pressure downstream from the valve 10 is greater than pressure upstream from the valve, the membrane 36 flexes outward to a position in which the outboard edge of the membrane seals against the band 20 as shown in FIGS. 2 and 7. In this membrane configuration, the valve 10 is closed. As will be appreciated by those skilled in the art, the valve configuration described above permits the membrane to seal against the band regardless of whether the native valve site is round. Thus, unlike native heart valves, which can leak excessively when the vessel in which they are positioned ovalizes, the valve of this design fully seals when the valve closes regardless of the shape of the passage in which it is positioned.

Although the valve 10 may have other dimensions, some valves have a height in a range from about 10 mm to about 20 mm. Further, some valves have a height in a range of about 15 mm to about 20 mm. Still further, some valves 10 are assembled so they have an opening at the junction of the struts 30, allowing a small amount of blood to flow through the valve 10 when closed to prevent stasis inside the leaflet unit 14, which might favor blood clot formation. As will be appreciated by those skilled in the art, blood clots are undesirable because once formed, the clots may break free and migrate to areas where they can cause damage such as stroke.

Over time (e.g., about 3 to 6 months), the band 20 integrates with the heart tissue forming the passage, and blood flowing through the valve infuses the struts 30 and membrane 36 with cells. As a result, the regenerative material essentially becomes patient tissue and has a lifespan equivalent to surrounding patient tissue. It is believed that this characteristic makes valves of the present invention particularly suitable for implant in pediatric patients because the valves become integral with patient tissue and are capable of expanding to fit the growing child. Further, because the valve 10 has a membrane that deflects inward toward the axial centerline of the valve rather than cusps that flex outward, the relative potential flow area through the valve is potentially larger than flow areas through similarly sized native heart valves having cusps. As a result, it is envisioned that functioning valves may be made in smaller sizes while retaining sufficient flow characteristics.

The replacement valve may be positioned in and attached to the heart H using any suitable technique. The collar 12 is sutured entirely around the passage to hold the valve 10 in place and in contact with the heart tissue.

It is noted that positioning most of the regenerative heart valve in the left and right atrium may be beneficial in that it avoids customary intraventricular placement which can impair normal ventricular biomechanics.

It is envisioned that the regenerative valve 10 described above may be used in several valve applications. For a first example, the valve 10 may be used to replace a mitral valve to control functional ischemic mitral valve regurgitation or other failures. In a second example, the valve 10 may be used as a vena cava venous valve to control tricuspid valve regurgitation in late stage right heart failure. In this second example, the valve may be implanted as indicated either to the inferior vena cava below the hepatic veins of the right atrium, or into the superior vena cava above its junction with the right atrium. In a third example, the valve 10 may be used to correct calcific aortic valve stenosis or combined stenosis/regurgitant disease.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A replacement valve for replacing a damaged heart valve having a plurality of cusps separating an upstream region from a downstream region of a passage, said replacement valve comprising:
    a flexible band including biocompatible scaffolding sized for contact with a wall surrounding the passage in the patient's heart;
    a resilient element attached to said flexible band for expanding said flexible band to contact the wall of the passage;
    a plurality of regenerative struts spaced around the flexible band, each strut extending from an outboard end joined to an inward face of the flexible band to a central end, the central ends of said plurality of struts being joined together; and
    a flexible regenerative membrane joined to adjacent pairs of said plurality of struts, said membrane extending outboard to an inward face of the band, an outboard edge of said membrane being free to move between a closed position in which the membrane abuts the inward face of the band to prevent fluid flow past the membrane and an open position in which the outboard edge of the membrane is spaced from the inward face of the band to permit fluid flow past the membrane.

2. A replacement valve as set forth in claim 1, wherein the membrane has a thickness in a range of about 0.005 inches to about 0.010 inches.

3. A replacement valve as set forth in claim 1, wherein the flexible regenerative membrane is unitary and joined to each adjacent pair of said plurality of struts.

4. A replacement valve as set forth in claim 1, wherein the flexible regenerative membrane is shaped as a cone.

5. A replacement valve as set forth in claim 4, wherein the cone has a perimeter at a base at least as large as a perimeter of the inward face of the band.

6. A replacement valve as set forth in claim 1, wherein the flexible regenerative membrane comprises decellularized small intestinal submucosa extracellular matrix derived from an animal.

7. A replacement valve as set forth in claim 1, wherein the flexible regenerative membrane comprises a bioscaffold tissue including regenerative cellular and matrix components derived from mesenchymal bone marrow patient stem cells.

8. A replacement valve as set forth in claim 1, wherein the membrane, the flexible band, and the plurality of regenerative struts are constructed using resorbable sutures.

9. A replacement valve for replacing a damaged heart valve having a plurality of cusps separating an upstream region from a downstream region of a passage, said replacement valve comprising:
- a flexible band including biocompatible scaffolding sized for contact with a wall surrounding the passage in the patient's heart;
- a plurality of regenerative struts spaced around the flexible band, each strut extending from an outboard end joined to an inward face of the flexible band to a central end, the central ends of said plurality of struts being joined together; and
- a flexible, cone-shaped, regenerative membrane joined to adjacent pairs of said plurality of struts, said membrane having an outer edge sized to correspond with an inward face of the band, at least portions of the outer edge of said membrane being free to move between a closed position in which the membrane abuts the inward face of the band to prevent fluid flow past the membrane and an open position in which the outer edge membrane is spaced from the inward face of the band to permit fluid flow past the membrane.

10. A replacement valve as set forth in claim 9, wherein the membrane has a thickness in a range of about 0.005 inches to about 0.010 inches.

11. A replacement valve as set forth in claim 9, wherein the flexible regenerative membrane is unitary and joined to each adjacent pair of said plurality of struts.

12. A replacement valve as set forth in claim 9, wherein the outer edge of the membrane has a perimeter at least as large as a perimeter of the inward face of the band.

13. A replacement valve as set forth in claim 9, wherein the flexible regenerative membrane comprises decellularized small intestinal submucosa extracellular matrix derived from an animal.

14. A replacement valve as set forth in claim 9, wherein the flexible regenerative membrane comprises a bioscaffold tissue including regenerative cellular and matrix components derived from mesenchymal bone marrow patient stem cells.

15. A replacement valve as set forth in claim 9, wherein the membrane, the flexible band, and the plurality of regenerative struts are constructed using resorbable sutures.

\* \* \* \* \*